United States Patent [19]

Amazeen et al.

[11] 4,431,007

[45] Feb. 14, 1984

[54] REFERENCED REAL-TIME ULTRASONIC IMAGE DISPLAY

[75] Inventors: Paul G. Amazeen, Folsom; Patrick L. Sutcliffe, Citrus Heights, both of Calif.

[73] Assignee: General Electric Company, Schenectady, N.Y.

[21] Appl. No.: 231,526

[22] Filed: Feb. 4, 1981

[51] Int. Cl.³ ............................................. A61B 10/00
[52] U.S. Cl. ....................................... 128/660; 73/626
[58] Field of Search ................................ 128/660–663; 73/726; 358/38, 112

[56] References Cited

U.S. PATENT DOCUMENTS 4,109,642  8/1978  Reid et al. ......................... 128/663
4,209,022  6/1980  Dory .................................... 128/660
4,236,221  11/1980  Cribbs et al. ................... 128/660 X

OTHER PUBLICATIONS

Ophir, J. et al., "Digital Scan Converters in Diagnostics UTS Imaging", Proc. of the IEEE, vol. 67, No. 4, Apr. 1979, pp. 654–664.

*Primary Examiner*—Kyle L. Howell
*Assistant Examiner*—Francis J. Jaworski
*Attorney, Agent, or Firm*—Wheeler, House, Fuller & Hohenfeldt

[57] ABSTRACT

Either a linear array ultrasound transducer or a phased array transducer is constrained to scan along a body in a single plane to derive data for enabling simultaneous display of static and real-time ultrasound images.

2 Claims, 11 Drawing Figures

REFERENCED REAL-TIME ULTRASONIC IMAGE DISPLAY

BACKGROUND OF THE INVENTION

This invention relates to apparatus that uses ultrasound to produce images of a section of an object such as the human anatomy.

B-scans and real-time scans are among the ultrasound apparatus operational modes for obtaining images. In the B-scan mode, a transducer, usually a single piezoelectric crystal, is moved along the body surface in a single plane while the transducer emits a pulsed beam of ultrasound and receives echos from wherever there are density discontinuities or impedance changes in the body as is well known. The echo energy is converted by the transducer to electric signals which can be organized in a manner that enables an image of the plane that is traversed by the beam to be reconstructed or displayed. B-scanners support the transducer on an arm assembly of two or three pivotally connected segments which constrain the transducer to move in a single plane, so the reconstructed image is a view of a slice through the anatomy.

The arm segments are provided with position-sensing elements for providing data indicative of the origin and the direction of any beam originating from the transducer. If the transducer is periodically excited and the reflected data is stored in a memory array at locations corresponding to the position of the transducer at the time of the pulse, then, as the transducer is moved along the body, the echo data will fill the array to provide a final composite picture.

In systems to which the present invention is pertinent, the echo signals representative of picture elements (pixels) for a single ultrasound scan, after suitable processing and digitization, are stored in a memory array. The memory array and its affiliated controls provides for converting the digital pixel signals to analog video waveforms on a line-by-line basis to enable displaying the image on a cathode ray tube screen. B-scanning is not, however, suitable itself for picturing moving parts of the anatomy, such as the heart, which is in motion due to beating or the thorax which is in motion due to breathing.

Real-time imaging is now accomplished by using a linear array to form a rectilinear image, or using a mechanically oscillated or rotated transducer(s) to form a sector image or using a phased array transducer to electronically steer the ultrasound beam to form a sector image. In all of these methods ultrasound beams are directed through a region of the anatomy at a rate sufficiently fast to make the continually updated echo data appear live in the display. As is well known, linear array transducers are composed of a series of juxtaposed similar piezoelectric elements on the order of about 64 elements, for example. The elements are pulsed with high voltage in some orderly and repeatable sequence to cause them to emit ultrasound pulses that result in corresponding echo signals which are addressed to the scan converter memory array and are continuously updated or refreshed at a high rate so a real-time or motion-indicating image can be displayed.

A significant deficiency in prior art real-time scanning systems is that only an image of a slice of anatomy which is under the transducer is displayed. When the transducer is moved along the body surface to obtain an image of an adjacent region in the anatomy, the previous image disappears from the display. Thus, the viewer must exercise judgment, based on general knowledge of anatomy, as to where any image is located in the anatomy. In other words, there is nothing to which the real-time image on the display can be referenced to determine its location more exactly relative to surrounding anatomy. For instance, a sector scan transducer might be rocked or a linear array transducer might be scanned along a body in search of a tumor which, when located, the physician might want to palpate and observe in real-time on the display screen. In such case it would be desirable if the physician were able to observe where the tumor is located relative to other parts of the anatomy. Heretofore, it has not been possible to do this on a single display screen. The difficulty is accentuated where, as on many occasions, the person who made the scan and recorded it is not the same as the person who must display it and interpret it at a later time. Having a real-time or active region embraced by static views of surrounding anatomical regions would be particularly valuable under these circumstances. Moreover, real-time images are more likely to be misinterpreted at any time that the interpreter is not positive about where the image has been taken.

SUMMARY OF THE INVENTION

An object of this invention is to provide an ultrasound examination system which enables a real-time image, corresponding with the present location of a linear array or sector scan transducer to be displayed, and which when the transducer is moved in either direction, continues to display static images of anatomy contiguous with a real-time image all on the same display device.

Briefly stated, for the purposes of the invention, a linear array or, alternatively, a sector scan transducer is mounted at the end of the distal arm member of an articulated arm assembly comparable to the type now used in B-scan apparatus, so the transducer is constrained to move in the single plane of the arm assembly during a scan. The center of the transducer is coincident with the end of the distal arm member which is thus perpendicular to the plane of the transducer.

When a linear transducer array is used, the individual piezoelectric elements are pulsed through a slice of anatomy undergoing the real-time part of the scan. The signals resulting from echos returned by density discontinuities in the anatomy are stored for the duration of one pulse cycle at least in the memory of a scan converter as is basically comparable to what is done in some existing apparatus that is adapted for making B-scans and real-time scans.

In conventional B-scan apparatus, information about the angles of the extensible and contractible transducer support arm is obtained by devices that provide signals corresponding with the sines and cosines of the angles of the arm members, which allows the X and Y coordinates of the transducer to be calculated. The angle information is used to calculate the starting point and the slope for a vector through the scan converter memory array so that echo signals representative of impedance changes or discontinuities in the anatomy will be addressed to locations in the memory array corresponding with locations in the slice of anatomy being scanned.

In accordance with the invention, however, means are also employed to provide position information on each transducer element in the array at the time it is pulsed, or, if a sector scan transducer is used, to provide information as to its angles in correspondence with the pulses. In actuality, means are provided for obtaining a vector which is aligned with and starts from the center of the transducer that is in use and is either translated or rotated in the plane normal to the plane of the articulated scan arms, according to whether a linear array or a sector transducer is being used, by a constantly changing amount as the transducer is pulsed, which modifies the storage location of the echo signals in the memory array. location of the echo signals in the scan converter array is concerned. As the transducer moved some storage locations in the memory array are no longer addressed and in that memory the echo signals from the preceding location of the transducer remain stored.

Thus, data for displaying a static image of these previously scanned locations is available.

How the aforementioned general object and other more specific objects of the invention are achieved will become apparent in the ensuing more detailed description of an illustrated embodiment of the invention which will now be set forth in reference to the drawings.

DESCRIPTION OF A PREFERRED EMBODIMENT

Figure 1:
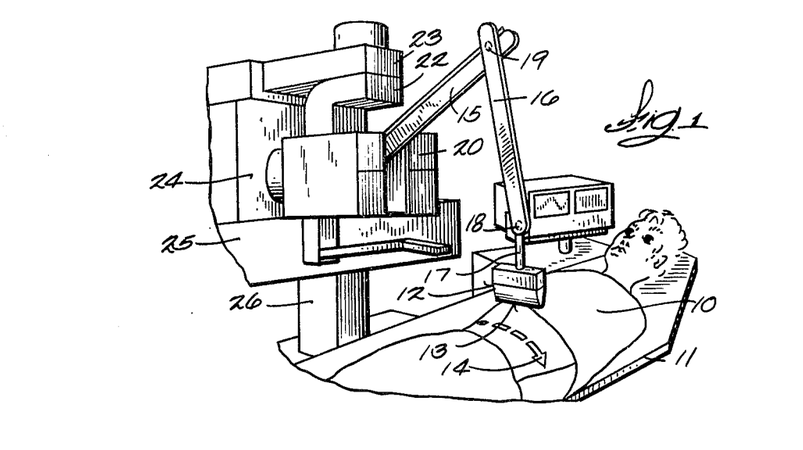
FIG. 1 is a partial perspective view of an ultrasound scanner that is adapted for displaying composite static and real-time images of a layer of the anatomy on a single display.

FIG. 1 shows a typical B-scan ultrasound scanner which has been adapted for displaying composite static and real-time images of a layer of the human anatomy on the same display screen in accordance with the invention. A real-time image is defined as one based on obtaining ultrasound echo data at a sufficiently high rate to enable depicting a part of the anatomy which is currently under the transducer and, possibly, moving without having to translate the transducer to assemble the data as is required in making an ordinary B-scan. Static image as used herein is defined as an image of a body layer over which the transducer was located prior to its present location where it is yielding a real-time image and the static image or images are contiguous with the real-time image in the display.

In FIG. 1 a patient 10 is supine on a table 11 in readiness for an ultrasound examination. A linear array transducer head 12 is positioned above the patient. The linear array of transducer elements is located in the bottom end of the head and is generally designated by the numeral 13. To perform a scan, the linear array will be placed in contact with the body surface of the patient 10 to scan in a straight line along a vertical plane or slice of the anatomy whose upper edge is defined by the dashed arrowheaded line 14, for example.

In FIG. 1, the transducer is supported on an articulated arm assembly comprised of a proximal arm 15, an intermediate arm 16 and a distal arm 17. Arm 17 is pivotally connected to arm 16 for turning about a horizontal axis 18. Arm 16 is connected to arm 15 for pivoting about a horizontal axis 19. Most inward or proximal arm 15 is mounted to a base member 20 for pivoting about a horizontal axis which is not visible in FIG. 1 but is identified by the numeral 21 in FIG. 5. For purposes which will appear later, and as shown in the FIG. 5 diagram, the length of proximal arm 15 between its pivots is called L1, the length of arm 16 is called L2 and the length of distal arm 17 is called L3. L3 is the total distance from pivot axis 18 to the center piezoelectric element in the linear array 13 of the piezoelectric transducer elements.

Referring to FIG. 1, base 20 is mounted to a member 22 which is, in turn, mounted to a translating carriage 23, for rotation about a vertical axis. During a scan, member 22 is presumed to be locked against rotation and the arm assembly is constrained to fold and unfold in a single plane to thereby translate the transducer linearly in the same plane. Member 23 is mounted to an upright member 24 which is supported for translation along a horizontal member 25 to enable the transducer to be positioned for moving along any selected vertical plane over the length of the patient's body. The apparatus is on a floor stand 26.

Figure 2:
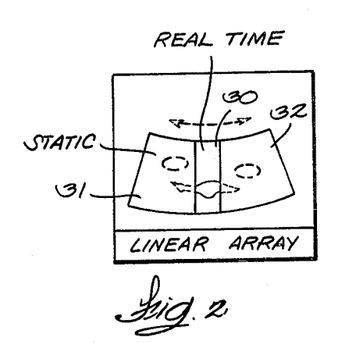
FIG. 2 is a diagrammatic view of the screen of a cathode ray tube displaying a composite static and real-time image obtained by scanning with a linear array transducer.

FIG. 2 illustrates the kind of image appearing on the display screen when a scan of a body layer is being made with a linear transducer, in accordance with the invention. The real-time image is shown as being in the center of the composite image in FIG. 2 and is marked 30. Static images 31 and 32 are contiguous with the real-time image. The real-time image has a width corresponding with the acoustic length of the transducer array. This part of the composite image is under the active transducer at the present time and would show the anatomy in motion, if motion existed, such as would be the case if the heart were in view. The static images 31 and 32 that are contiguous to real-time image 30, are images of the regions from which the transducer have been moved to reach its real-time position. Thus, there is always a static image segment visible which allows the examining physician to relate the actively scanned portion of the anatomy to surrounding anatomy. The location of any part of the anatomy can be even more accurately determined by referencing the starting point of a scan to a point on the body. For example, the umbilicus could be taken as a reference point and the start could be indicated as being so many centimeters up, down, left or right of the umbilicus.

Figure 3:
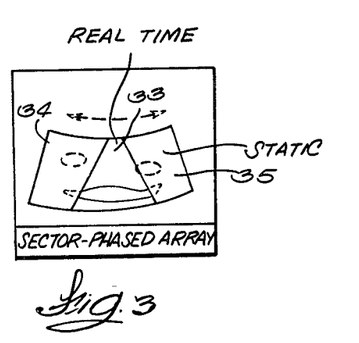
FIG. 3 is a diagrammatic view of a cathode ray tube displaying a composite static and real-time image obtained by scanning with a sector scan transducer.

FIG. 3 illustrates the composite static and real-time images obtained with a mechanical sector or phased array transducer in accordance with the invention. In this case, the transducer is either mechanically or electronically steered in a plurality of directions within an overall sector to produce the active or real-time segment marked 33 in FIG. 3. Again, there are static images 34 and 35 of the anatomy surrounding or contiguous with the real-time segment.

Figure 5:
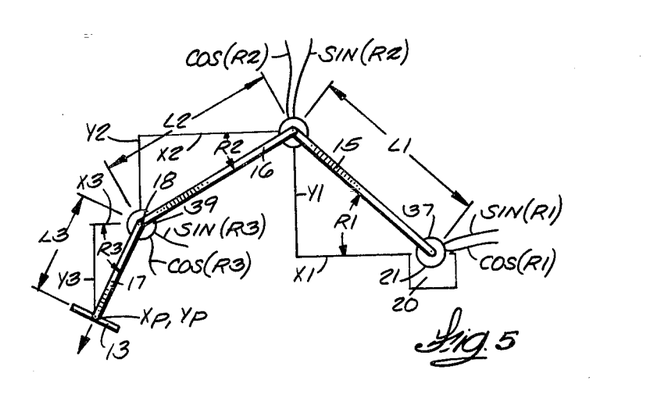
FIG. 5 is a diagram of an ultrasound scanner arm assembly having its angles and dimensions labelled to facilitate an explanation of the invention.

A diagram of the articulated arm assembly is shown in FIG. 5. The linear array transducer 13 is represented by a straight line to which the distal arm 17 is perpendicular. The point marked Xp,Yp are the coordinates or the center of the transducer array or, in other words, the coordinates of the center piezoelectric element and the surface thereof which contacts the body.

Figure 6:
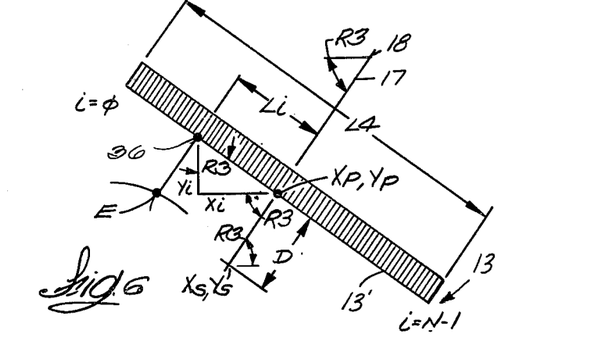
FIG. 6 is a diagram of a linear array transducer attached to the distal segment of the scanner arm assembly.

A linear piezoelectric element array is shown diagrammatically in FIG. 6. The length of the array is specified as L4. The length is divided by a plurality of juxtaposed lines and the space between each pair of lines symbolizes what is herein called a piezoelectric transducer element. It should be understood, however, that an element typically comprises a group of smaller juxtaposed piezoelectric crystals which are activated or used in concert. In some designs the ultrasound pulses are transmited into the body and the echos are received by the same transducer element. The same crystals within an element are not necessarily used to transmit and receive and, in particular, the number of small crystals in a receiving sub-group is usually changed (for a single transmitted ultrasound pulse) during the reception of echos from varying positions within the body under examination. However, the vector extending from an element, corresponding to the display vector, will be centered in the group of small crystals comprising an element. Thus, for derivations which will be presented later, it is appropriate to express distances along the array in terms of the distance from the center of the array to the center of any particular element. Since the vectors are centered with an element, the linear array does not produce an image that is fully as wide as the actual physical length of the transducer array.

During a scan, high voltage pulses are applied to the transducer elements in a predetermined order thereby to cause them to transmit ultrasonic beams into the anatomy. As is known, as soon as a pulse of sound energy is emitted, the active element (using element broadly even though it may contain sub-groups) becomes a receiver of sound echos whose magnitudes are dependent on the impedance or density variations or discontinuities along the beam path. As is known, the depth of a discontinuity is determined by measuring the time that it takes for the sound beam to travel from and back to the active piezoelectric element. In FIG. 6, one discontinuity occurring along the beam emitted from a typical element 36 is marked E. The echo signals from these discontinuities must, of course, be arranged in an electronic memory array in a position which corresponds with their occurrence in the anatomy so that the data for producing an intelligible image in real-time can be maintained. Of course, position information for addressing echo data along proper vectors in the memory array is required in regular B-scanning and real-time scanning too. However, in prior art real-time scanning only the anatomy which is presently under the transducer is displayed, whereas, in accordance with the invention, anatomy contiguous with the real-time segment is also displayed so that the physician can accurately determine the location of the real-time segment relative to surrounding anatomy. The manner in which position information is developed so that static and contiguous real-time images can be displayed will now be described.

The system is based on delivering digital echo signals, representative of image or picture elements (pixels), to a scan converter memory array. The scan converter converts the signals to analog video waveforms to enable displaying the image on a television monitor. Typically, each memory location is 5 bits deep to allow for 32 shades of gray in the displayed pixels.

In the composite real-time and static imaging system constituting the invention, part of the transducer angle and position information required is similar to that which is required for a conventional B-scan in a scan converter system. The angle and direction of the transducer with respect to a reference point must be known in order to be able to address the echo data along a properly angulated and positioned vector in the memory array that corresponds with the angle and position of the ultrasound beams in the anatomy. In addition, to be able to provide a real-time image reference to a contiguous static image, in accordance with the invention, it is necessary to obtain position and angle information on each transducer element in the array as it is pulsed with high voltage.

Referring to FIG. 5, the articulated arm assembly constrains the linear array transducer to move in a single plane. To describe location of points within this plane, define horizontal and vertical axes such that X is the horizontal distance of a point away from the fixed base point 21 of the arm assembly and Y is the distance below the base point 21. Thus, any point in the plane can be described by an ordered pair, (X,Y), with the origin at the fixed point 21 where X=0 and Y=0. The position (Xp,Yp) that corresponds to the location of the end of distal arm 17 and the center element in the linear array transducer 13 can be determined by summing the X and Y components of arms 15, 16 and 17 which are treated as vectors.

The three arms comprising the arm assembly in this example, have known lengths L1, L2 and L3 between their pivot points as shown. The angles between the arms and the horizonal are labelled R1, R2 and R3, respectively. Then $$Xp = X1 + X2 + X3 \text{ and}$$

$$Yp = Y1 + Y2 + Y3$$

By vector component addition and where an asterisk indicates multiply:

$$Xp = L1 * \cos(R1) + L2 * \cos(R2) + L3 * \cos(R3) \quad \text{Eq. (1)}$$

$$Yp = L1 * \sin(R1) + L2 * \sin(R2) + L3 * \sin(R3) \quad \text{Eq. (2)}$$

As illustrated in the FIG. 5 diagram, signals having values proportional to the sines and cosines of arm angles R1, R2 and R3 are developed with sine-cosine potentiometers 37, 38, and 39. This is a symbolic representation of the potentiometers. In reality they may be located in the base 20 and may be driven with pulleys and cables, not shown. Linear potentiometers that provide signals directly proportional to angle could also be used provided the signals are converted to sine and cosine functions before they are used in the calculations.

FIG. 6 shows the linear array of piezoelectric transducer elements wherein the first element is designated $i=0$ and the last element $i=N-1$ where N is the number of elements. Typically, there would be a minimum of $N=64$ elements in an array making up a total length L4 of about 10 cm. As mentioned earlier these elements are symbolized as being constituted by a single piezoelectric element while, in fact, they may consist of sets of elements centered about the symbolic element. An ultrasound beam transmitted by applying a high voltage pulse to any symbolized transducer element at an initial time T0 will produce echos from discontinuities in the anatomy which return to the element at a time $T1=T-T\emptyset$. For present purposes, the piezoelectric elements are pulsed in a selected repeatable order or cycle. A frame synchronization pulse initiates selection of the first element in a cycle and a vector synchronization pulse causes the selected element to be pulsed with high voltage and the element selection to be advanced to the next element. The frame synchronization pulse and the first vector synchronization pulse in a cycle coincide in time and the remainder of the vector synchronization pulses follow. 3000 pulse cycles per second is typical. The sound frequency will customarily be in the range of 2 MHz to 20 MHz with about 3 MHz being most common.

In FIG. 6, if the distance to any anatomical discontinuity or echo point from the transducer element position (Xp,Yp) is D, then T1 corresponds to the time for the ultrasound pulse to travel a distance 2*D down to the point and back to the transducer, at the speed of sound, C, within the medium. Therefore, $$T1 = 2*D/C \text{ or}$$

$$D = (C/2)*T1$$

As is evident in the FIG. 6 diagram, the sound energy is transmitted from and reflected back to a transducer element along a line that is perpendicular to the front face 13' of the transducer element array 13. Assume that there is an echo producing impedance discontinuity at the point identified by the coordinate Xs,Ys at a distance D from a transducer element in line with distal arm segment 17. When the sonic energy wave front reaches this point it will be at a definite X distance and Y distance from the point Xp,Yp at the center of the array. It will be evident, however, that the X and Y components or distances will be constantly changing because the wave front goes out and returns. For present purposes it is necessary to determine the rate of change in the X and Y component lengths or distances of the wave front relative to Xp,Yp. First an expression for the location of the point is determined.

$$Xs - Xp = D* \text{Cos}(R3)$$

$$Ys - Xp = D* \text{Sin}(R3)$$

Since $D = C/2*T1$ $$Xs - Xp = (C/2)* \text{Cos}(R3)*T1$$

The rate of change of the X coordinate is the change in the X per unit time so, $$X \text{ change} = (Xs - Xp)/T1 \quad \text{Eq. (3)}$$

$$= (C/2) * \text{Cos}(R3)$$

and similarly the rate of change of the Y coordinate is, $$Y \text{ change} = (Ys - Yp)/T1 \quad \text{Eq. (4)}$$

$$= (C/2) * \text{Sin}(R3)$$

For the purposes of the invention, the reflected echo data is delivered to an electronic memory array which accumulates the data for each transducer pulsing cycle to enable reconstructing a visible live or real-time image segment of the slice of anatomy which is presently under the transducer array and contiguous static image segments of slices over which the array was located prior to reaching the real-time location. How the memory connects into the system will be discussed later.

It will be evident that picture element (pixel) data must be written into the memory locations in the same orientation as it is generated in the body. How it is written depends on the angular attitude of the array 13 of transducer elements and the distance of the array from base point 21 of the transducer support arm assembly. For any angular attitude, the transducer elements are activated in a predetermined order to transmit sound and receive echo pulses lying along vectors that are perpendicular to the faces of the respective elements. The system to be described produces a first vector synchronization (sync) pulse for each scan or sweep across the array and further vector synchronization pulses for each of the elements in the array in sequence. The first vector sync pulse in a scan cycle is also a frame sync pulse which indicates that a scan cycle or frame is beginning.

Storage in the memory uses a scaled and offset coordinate system. The memory array has storage locations corresponding to positions that the transducer and its elements can be in along the plane or slice in which the transducer is constrained to move by the arm assembly on which it is mounted. For a given set of collected echo or pixel data, the storage segment is offset anywhere within the available area and can be scaled arbitrarily. We let K be the scaling factor such that two adjacent array locations correspond to a unit of distance. Then the rates of change of the memory array coordinates are $$X \text{ rate} = K * X \text{ change} \quad \text{Eq. (5)}$$

$$= K * (C/2) * \text{Cos}(R3)$$

$$= K1 * \text{Cos}(R3)$$

and $$Y \text{ rate} = K * Y \text{ change} \quad \text{Eq. (6)}$$
$$= K * (C/2) * \text{Sin}(R3)$$

$$= K2 * \text{Sin}(R3)$$

K1 and K2 may not be equal if the memory array coordinates are not square. For instance, if the display of the memory pixel data contents is on a television monitor, the memory array will usually be made rectangular by the ratio of 4:3 to compensate for the 3:4 aspect of the television display monitor.

Equations (1) and (2) provided an expression of the coordinates Xp,Yp of the center of the transducer element array. The system described herein requires an expression of the location of each symbolized transducer element with respect to the center and an expression of the start point position for a cycle of pulses when a linear array transducer is used in order to enable electronic implementation.

Referring to FIGS. 5 and 6, the linear array of elements 13 is perpendicular to the distal support arm segment 17 and aligned so each element lies in the plane of the articulated arm. The end elements selected for pulsing following a frame sync pulse are assigned i=0. The parameter i indexes the start point vector position change and is incremented by vector sync pulses. In FIG. 6, let L4 be the known length between the first and last vector start points in the linear array and let N be the number of discrete start points within the array. Then the separation between adjacent start points is $$Ls = L4/(N-1)$$

and the separation of the ith position from the center is $$Li = (L4/2) - i*Ls$$

In FIG. 6 one may see that the displacement of an element at the time of its vector sync is $$Xi = Li * \text{Sin}(R3)$$

$$= \left(\frac{L4}{2} - i*\frac{L4}{N-1}\right) * \text{Sin}(R3)$$

$$= \frac{L4}{N-1} * \left(\frac{N-1}{2} - i\right) * \text{Sin}(R3)$$

and $$Yi = -Li * \text{Cos}(R3)$$

$$= -\left(\frac{L4}{N-1}\right) * \left(\frac{N-1}{2} - i\right) * \text{Cos}(R3)$$

Now, modifying equations (1) and (2) to find the coordinate Xpi,Xpi of the actual start point position and referring to FIGS. 5 and 6, $$Xpi = Xp + Xi \qquad \text{Eq. (7)}$$

$$= L1 * \text{Cos}(R1) + L2 * \text{Cos}(R2) + L3 * \text{Cos}(R3) +$$

$$\left(\frac{L4}{N-1}\right) * \left(\frac{N-1}{2} - i\right) * \text{Sin}(R3)$$

and $$Ypi = Yp + Yi \qquad \text{Eq. (8)}$$

$$= L1 * \text{Sin}(R1) + L2 * \text{Sin}(R2) + L3 * \text{Sin}(R3) -$$

$$\left(\frac{L4}{N-1}\right) * \left(\frac{N-1}{2} - i\right) * \text{Cos}(R3)$$

Equations (7) and (8) indicate how the start point at which a vector sync pulse occurs is translated from transducer element to transducer element during a pulsation cycle. As indicated earlier, as the transducer is moved, some storage locations in the memory array are no longer addressed and in that memory the echo signals from the preceding location of the transducer remain stored. It should be noted that regardless of which element is active, the X rate and Y rate of change as expressed in Equations (5) and (6) remains unchanged.

The manner in which the foregoing calculations are implemented to enable display of real-time and contiguous static ultrasound image segments on a single display when a linear array transducer 13 is used will now be discussed primarily in reference to FIG. 7. The sector scan transducer mode will be discussed later.

Figure 7:
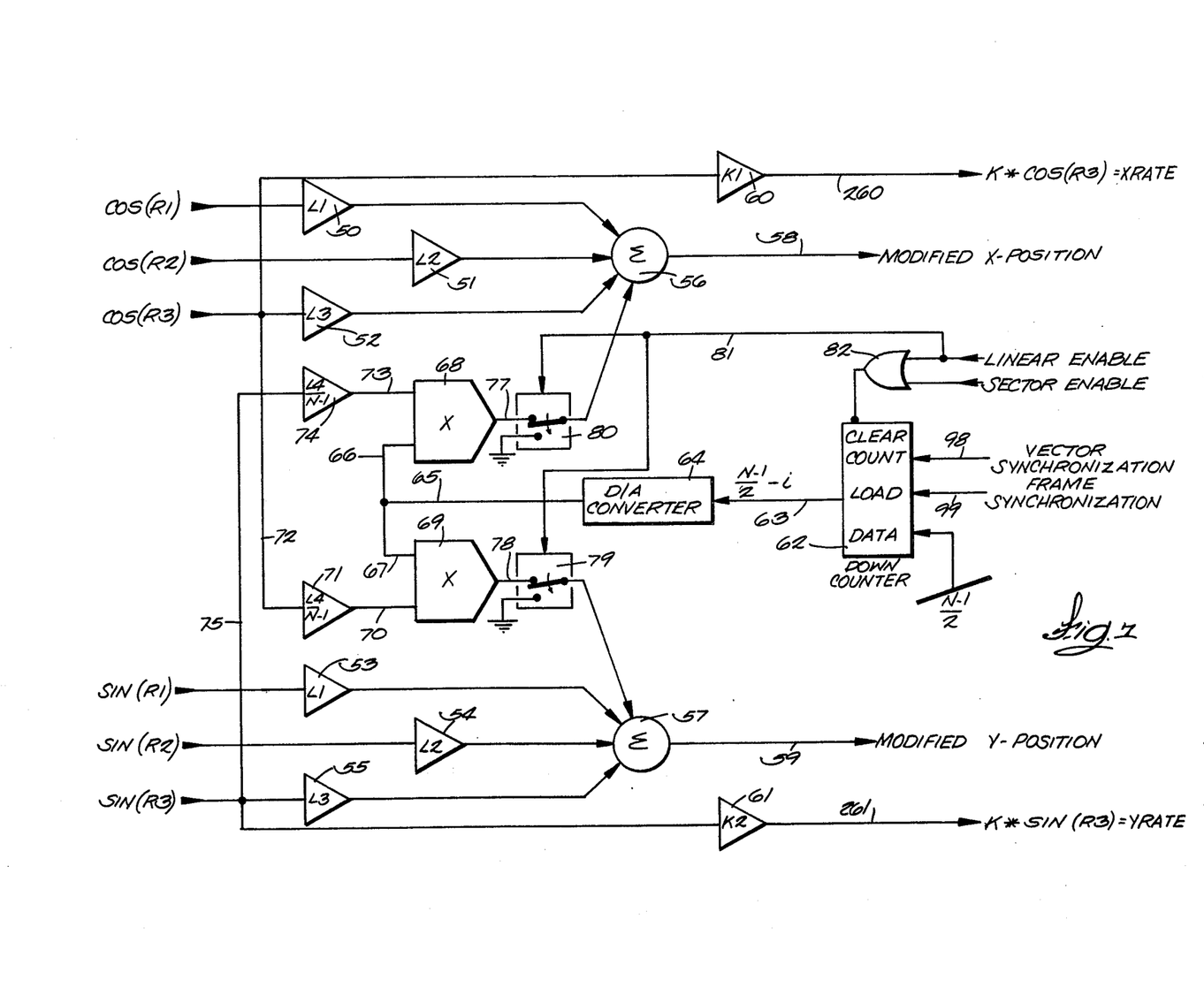
FIG. 7 is an electrical block diagram of a system that provides transducer element position information to the memory array storage controls for producing a composite static and real-time picture with a linear array transducer.

The six conductors entering from the left in the FIG. 7 diagram carry the analog signals representative of the sines and cosines of the support arm segment angles R1, R2 and R3 which are identified in FIG. 5 where sine-cosine potentiometers 37, 38 and 39 are shown. In FIG. 7 the cosine signals for angles R1, R2 and R3 are multiplied or amplified in amplifiers 50, 51 and 52, respectively, in correspondence with the arm segment length L1, L2 and L3 to which the angles pertain. The three sine signals for angles R1, R2 and R3 are similarly amplified in correspondence with the arm lengths in amplifiers 53, 54 and 55. The output signals from cosine amplifiers 50, 51 and 52 are summed in a summing device 56 and the output signals from sine amplifiers 53, 54 and 55 are summed in a device 57. The output signal from summer 56 on line 58 represents the X position of point Xp, Yp and the output signal from summer 57 on line 59 represents its Y position relative to the arm base point 21 as shown in FIG. 5. Thus, Equations (1) and (2) are realized. These position signals are, however, to be modified to indicate the position of the transducer element that is active at any time.

In FIG. 7 amplifiers 60 and 61 scale the Cos(R3) and Sin(R3) signals, respectively, in proportion to constants K1 and K2 which have been selected to produce the desired data shift along a vector in the memory array which was alluded to earlier. Thus, amplifiers 60 and 61 are operative to produce signals corresponding to X rate and Y rate, respectively, and Equations (5) and (6) are realized. The circuit operations described up to this point are comparable to those found in some preexisting B scanners where a single transducer element is moved along a body surface to accumulate echo signals for imaging a slice through the anatomy. Imaging with a linear array transducer and providing for displaying real-time and static images simultaneously, in accordance with the invention, requires, among other things inputting an additional term to each of the summers 56 and 57 so that the Xpi and Ypi positions of each element in the linear array transducer can be obtained. Hence, the X position and Y position signals on line 58 and 59, respectively, are modified.

Development of the additional term for the summers starts with a down counter 62 in FIG. 7. Vector sync and frame sync pulses are supplied to the counter as indicated. Occurrence of a frame sync pulse presets counter 62 to $(N-1)/2$. Each successive vector sync pulse clocks the down counter to produce a digital output corresponding to $(N-1/2-i)$ where i is the separation of the transducer element from the center as brought out in connection with development of Equations (7) and (8). At zero, the counter in this embodiment overflows to full scale and continues counting down until the next frame sync pulse occurs. The counter length must exceed N, the number of transducer start points.

The counter 62 digital output signals are delivered by way of a line 63 to the input of a digital-to-analog (D/A) converter 64. The analog output signals from converter 64 are delivered by way of line 65 to an input 66 of a multiplier 68 and an input 67 of a multiplier 69. One of the inputs 70 of multiplier 69 receives an analog signal corresponding to Cos (R3) amplified by the amount $L4/(N-1)$ by an amplifier 71. The Cos (R3) signal is inputted to amplifier 71 by way of line 72.

Similarly, the second input 73 to multiplier 68 receives an analog signal corresponding to Sin (R3) amplified by the amount $L4/(N-1)$ by an amplifier 74. The Sin (R3) signal is inputted to amplifier 74 by way of line 75. Thus, the analog output signals from converter 64 are multiplied by the scaled terms $L4/(N-1)*$ Sin (R3) and $L4/(N-1)*$ Cos (R3) to yield the terms $$L4/(N-1) * Sin(R3) * \left[ \frac{(N-1)}{2} - i \right]$$

on the output 77 of multiplier 68 and, $$L4/(N-1) * Cos(R3) * \left[ \left(\frac{N-1}{2}\right) - i \right]$$

on the output 78 of multiplier 69.

The output signals from multipliers 68 and 69 are summed, respectively, with other terms in summers 56 and 57 so that the output signals on lines 58 and 59 represent the modified X-positions and Y-positions of the transducer elements. Thus, Equations (7) and (8) are realized and the start position is determined. Note in Equation (8) that the output of multiplier 69 indicated above is actually substracted from the other terms inputted to summer 57. Hence, sign inversion is required and it could be accomplished with an inverter, not shown, before the input to summer 57 or it could take place in amplifier 71.

The circuit arrangement in FIG. 7 still permits using the ultrasound apparatus to make ordinary B-scans. For making B scans, of course, a single element ultrasound transducer head, not shown, would be substituted for the linear array transducer. For making B scans or sector scans, the sound pulses do not have to be incremented along an element array so only the unmodified X-position and Y-position (Xp,Xp) indicative signals need to be used. A satisfactory way of doing this is to switch the outputs 77 and 78 from multipliers 68 and 69, respectively, to ground. Semiconductor switches symbolized by the blocks marked 79 and 80 are provided to do the switching. Switches 79 and 80 would select the multiplier 68 and 69 outputs if the linear array transducer were in use and enabled or select ground if the array were not enabled. When a linear array enable signal is provided from a suitable control signal source, not shown, the signal is coupled by way of line 81 to the semiconductor switches 79 and 80 causing switching off of ground as indicated. An OR gate 82, having inputs for a linear array transducer enable signal and a sector scan transducer enable signal, is provided. The OR gate causes counter 62 to stop only if neither the sector mode nor linear scan mode is being used, since the counter output is needed during sector mode to modify the values of X-rate and Y-rate.

Now that the manner in which the geometrical data is obtained has been described, use of this data in conjunction with the echo data will be discussed in reference to the block diagram of the complete system depicted in FIG. 4.

Figure 4:
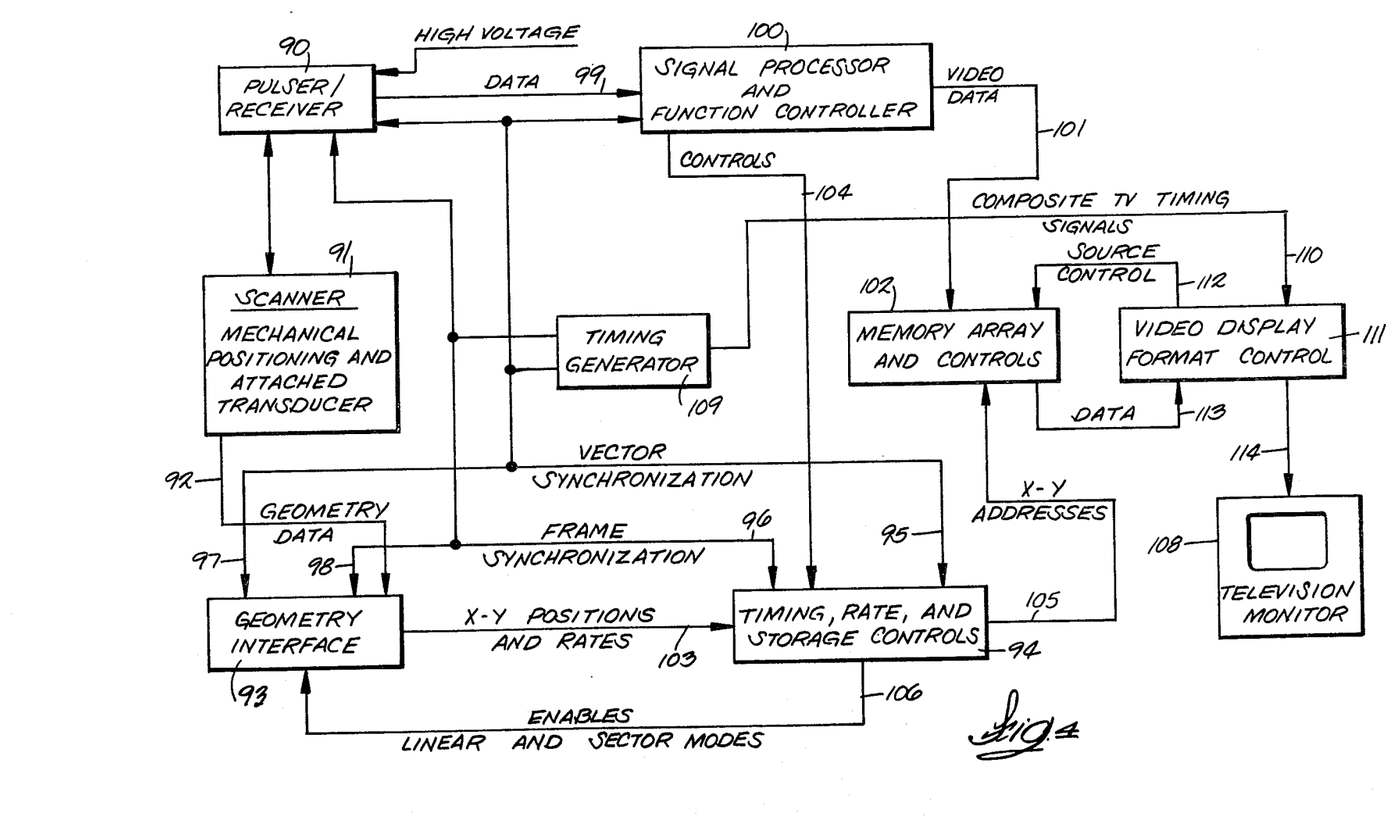
FIG. 4 is a block diagram of the electronic system for practicing the invention.

In FIG. 4 the basically conventional ultrasound pulser/receiver electronics are symbolized by the block marked 90. This block applies high voltage pulses to the transducer elements in the proper order to cause the elements to transmit ultrasound energy and between each transmitted pulse it receives echo signals or data from various depths in the body being examined.

The next block 91 symbolizes the scanner including the articulated arm assembly, the sine-cosine potentiometers 37-39 and the linear array transducer 13 that are all shown diagrammatically in FIG. 5. The geometry data, in particular analog signals corresponding to the sines and cosines of the angles R1-R3 are outputted on a multiconductor cable 92 to the geometry interface block 93. The contents of this block are depicted in FIG. 7 which has been discussed.

A block 109 is marked with the legend "Timing Generator." This block contains a timing pulse generator or clock, not shown. One function of this block is to put out the frame synchronization and vector synchronization pulse signals on bus conductors 95 and 96. These pulse signals are fed to various places such as to geometry interface 93 by way of lines 97 and 98 which are similarly marked in FIG. 7. As explained earlier, the frame sync pulse occurs coincident with the first vector sync pulse to start the down counter 62 and subsequent vector sync pulses cause the counter to continue counting down or decrement for each transducer element in the linear array. The frame and vector sync signals are also supplied to the pulser/receiver 90 for controlling it to activate the individual linear array transducer elements in sequence at a rate corresponding to the vector sync pulse rate. Thus, the vector sync pulse signals keep the pulser/receiver 90 and the geometry interface down counter in synchronization to thereby permit the FIG. 7 components to determine the X and Y coordinates of the transducer element that is presently active.

The analog echo signal data representative of image pixels is transferred from pulser/receiver 90 by way of a bus 99 to a signal processor and function controller block or module 100. This block processes the analog signals such as by altering their dynamic range. It also converts the analog signals to digital signals. It also performs digital signal processing such as converting high frequency digital video to a clock frequency, converting data from high frequency to sample clock rate, rejecting noise and enhancing signals. The principal functions of block 100 just outlined are present in preexisting B-scan apparatus and need not be described in detail. For present purposes, it is sufficient to recognize that there is analog-to-digital conversion of the echo data in block 100 and that the digital signals correspond in magnitude to the intensity of the pixels.

The video data is outputted from signal processor 100 by way of a bus 101 to a block 102 which bears the legend "memory array and controls." The memory array was mentioned earlier as the site in which the digital pixel signals are assembled and stored in an order corresponding to the locations of the density discontinuities in the slice or plane of the anatomy which yielded the signals. In conventional B-scan imaging using a single element transducer in accordance with the prior art, the transducer head is the distal member of the support arm assembly. Thus, the angle of the arm member corresponds with the angle of the vectors along which the echo or pixel data is written or addressed into the memory array or matrix. The single element transducer is always aligned with the distal arm member. Only one vector was and had to be generated for any given momentary position and angle of the transducer. This prohibited performing real-time scans using a linear array transducer since there has to be a vector for each transducer element in the array and a plurality of vectors have to be changed as the position or angle of the array changes.

The timing, rate and storage controls module 94 in FIG. 4 is operative to generate addresses for addressing the digital video data coming into memory array 102 on bus 101 to the proper locations in the array along the vector which corresponds with the X,Y positions and angles of the transducer elements. One segment of the memory array is constantly being refreshed with the data associated with the present position of the linear array so a real-time display is obtainable. Other segments of the memory array retain the data developed when the linear array transducer was in positions contiguous with the present position of the linear array transducer so static images can be displayed contiguously and simultaneously. Details on the address generation process will be given later in reference to FIG. 11.

Module 94 is supplied with signals from the geometry interface 93 via bus 103 corresponding to the X,Y positions of the linear array transducer elements and to the rates of change of the reflected echos in the X and Y direction relative to the center of the linear array. How these signals have been developed has been explained in reference to FIG. 7. Signals for producing horizontal and vertical traces, comparable to scan lines across the memory array, are provided by signal processor module 100 via bus 104 to control module 94. This enables module 94 to determine real-time pixel crossings with vectors for enabling exact addressing of the pixels to the proper location in the memory array. The addresses generated in module 94 are provided by way of an address bus 105 to the memory array.

The linear and sector mode enable signals mentioned earlier in connection with FIG. 7 are also provided from module 94, due to manual selection, to the geometry interface module 93 via a bus 106.

Image display on a TV monitor 108 is accomplished in a fashion typical of display controllers. A timing generator 109 using vector sync pulses as a time base provides composite TV timing signals via a line 110 to a video display format control 111. The format control provides signals to the memory array 102 for reading out the pixel data on a line-by-line basis. The pixel data is obtained from the memory array via a bus 113. The data is converted to analog video waveforms and the composite timing signals are injected to form composite video signals which are delivered by way of a line 114 to the television monitor which responds by displaying the composite image in the memory array, that is, an image made up of real-time and static images.

Figure 11:
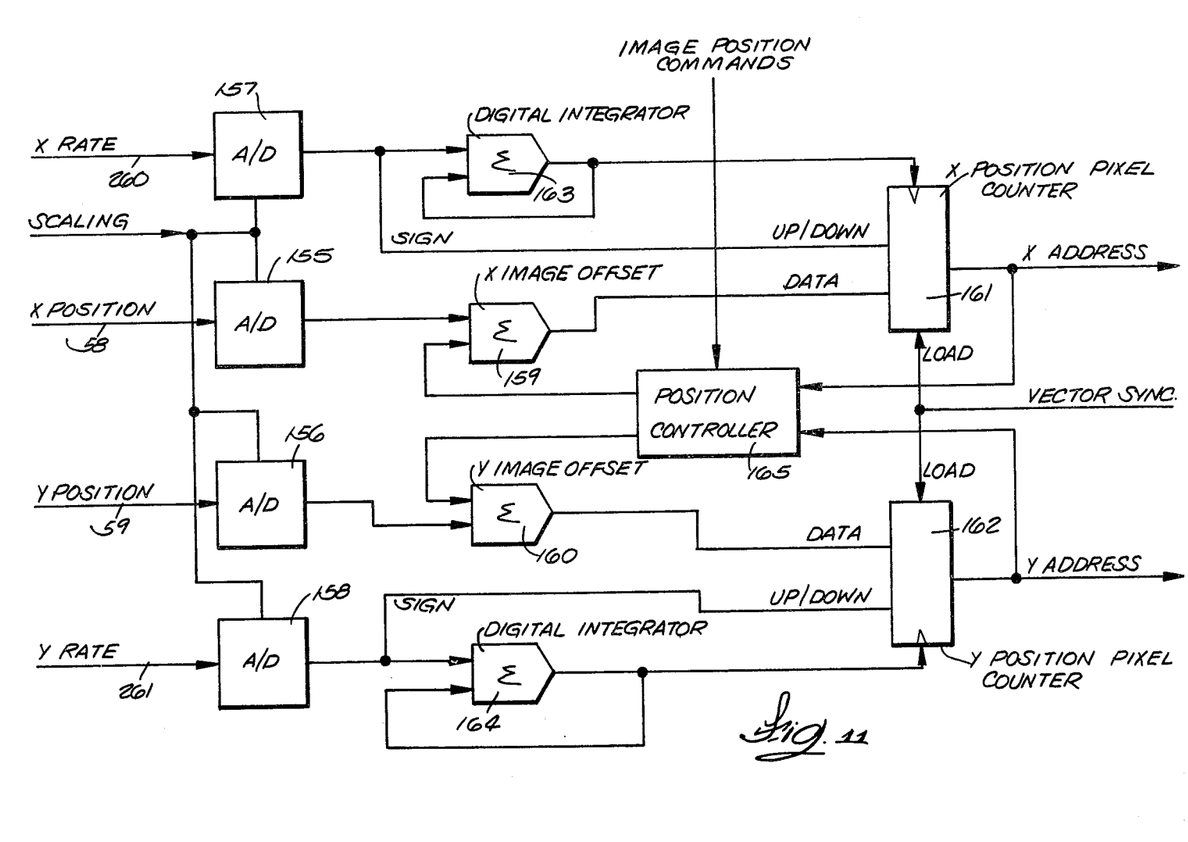
FIG. 11 is a diagram for explaining how rate and positional data is used to produce addresses which act on the memory array that is depicted in block form in FIG. 4.

The manner in which the rate and positional data is used to generate the addresses for getting the video data into the memory array 102 will now be discussed in reference to FIG. 11.

Prior to the start of each ultrasound vector the current values of the transducer X and Y position (from lines 58 and 59 in FIG. 7) and the current values of X rate and Y rate (from lines 260 and 261 in FIG. 7 or from summers 140 and 141 in FIG. 9 or from amplifiers 153 and 154 in FIG. 10) are converted by analog-to-digital converters 155–158. These A/D converters produce 12 bit outputs in this example that are a function of the selected image scaling as well as the individual inputs. The X and Y position outputs from converters 155 and 156 are added to the pixel displacements of the transducer elements from a mechanically calibrated reference point as previously explained. The digital position values are further offset by summers 159 and 160. Under control of a position controller 165, the summers can offset the position to any desired position, and should the offset equal the actual position the relative position output will correspond to the origin. The relative position values are presented as initialization data to position counters 161 and 162 in FIG. 11. At vector synchronization time this data is loaded into the counters 161 and 162 to provide the start point for echo signal storage.

The outputs of the other A/D converters 157 and 158 are input to digital integrators 163 and 164. These integrators (which function as voltage controlled oscillators) produce output pulses whose rates are proportional to the magnitudes of X rate and Y rate. Although the input, YRATE for example, represents the function Cos (R3), integration takes place in respect to time rather than over the angle R3. Sin (R3) represents the integral of Cos (R3) over the range of angles R3. Since the desired output is a pulse train whose rate or frequency is proportional to the input x-rate or y-rate, the actual function of the A/D converter and digital integrator pair is that of a voltage controlled oscillator. These outputs correspond to crossings of the memory array 102 location boundaries and, hence, are inputs to counters 161 and 162 to increment or decrement them to sequential address locations. Position counters 161 and 162 count either up or down, depending on the polarities of the rate inputs.

To summarize, at vector synchronization time the position counters 161 and 162 are loaded to the start addresses of the vector. These X address and Y address counters are then clocked at individual rates proportional to the rate inputs derived from the attitude or direction in which the transducer is aimed. These addresses assign the input echo signals to memory array locations.

In accordance with the invention, composite contiguous real-time and static ultrasound sector images are also obtainable by using a phased array scanner or transducer as previously alluded to in reference to FIG. 3. The phased array transducer is comprised of a plurality of transducer elements which are energized with time delays or phase shifts that results in ultrasound beams sweeping through an angle in a plane of the anatomy comparable to the manner in which the beam pulses would be projected if the transducer elements were rocked in a single plane about the point of contact with the body surface. A real-time sector image can also be produced with a mechanically rotated set of transducers, not shown, or with a single mechanically oscillated transducer.

Figures 8, 10:
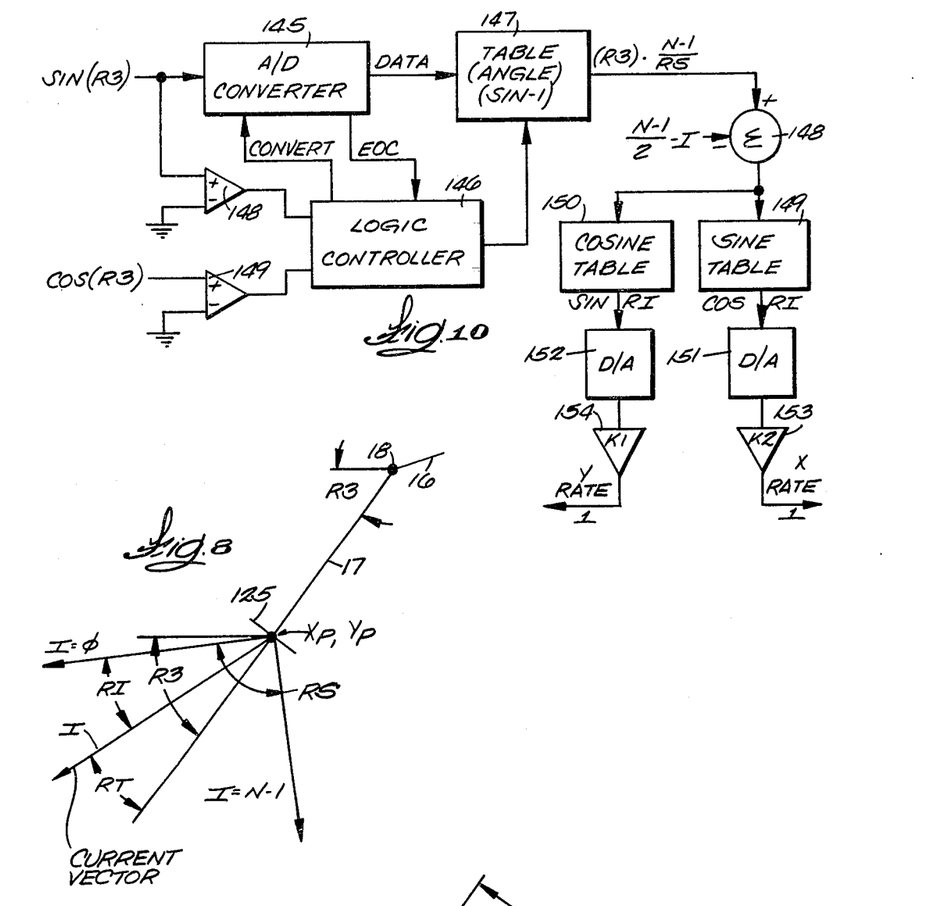
FIG. 8 is a diagram of a sector scan transducer attached to the distal segment of the scanner arm assembly with some angles being identified to facilitate description of composite static and real-time imaging.
FIG. 10 is an alternative to the FIG. 9 system.

The FIG. 8 diagram is for describing the sector scan mode for either a phased array or a mechanical sector scanner. The face of the transducer is represented by the line marked 125. The overall length of the transducer head constitutes the third or distal member of the arm assembly and is given the reference numeral 17 as was the same member in FIG. 5. In FIG. 8, the start point or center of the transducer is designated Xp,Yp as in the linear array transducer. Each time a vector synchronization pulse occurs, the direction of the sound beam changes by a discrete angular step. The transducer is aligned so these angular changes all occur in a single plane. The sine-cosine potentiometers 37–39 are not shown in the partial arm assembly in FIG. 8 but they are understood to be present.

In reference to FIG. 8, let the number of beams considered following a frame sync pulse be N. The total angle covered by the beams is RS. The angular difference between adjacent beams is RD such that $$RD = RS/(N-1)$$

Let the first vector following a frame sync pulse be at one end and correspond to I=0, where I is the beam index incremented by vector synchronization. Then the angle for the Ith beam (using angle designations of FIG. 5 for the arm members) is $$RI = R3 - \frac{RS}{2} + I*RD$$
$$= R3 - \frac{RS}{2} + I*\frac{RS}{N-1}$$
$$= R3 - \underbrace{\frac{RS}{N-1}*\left(\frac{N-1}{2} - I\right)}_{RT}$$

The only derived parameters affected by this angle change are X rate and Y rate, which control the direction through the memory array at which the echo data will be stored. If the actual angle is RI, then Equations (5) and (6) would be $$X \text{ Rate} = K1 \cos(RI)$$

and $$Y \text{ Rate} = K2 \sin(RI)$$

or $$X \text{ Rate} = K1 * \cos\left[R3 - \underbrace{\frac{RS}{N-1}*\left(\frac{N-1}{2} - I\right)}_{RT}\right] \quad \text{Eq. (9)}$$

$$Y \text{ Rate} = K2 * \sin\left[R3 - \underbrace{\frac{RS}{N-1}*\left(\frac{N-1}{2} - I\right)}_{RT}\right] \quad \text{Eq. (10)}$$

Let $R3 - RI = RT$, then $RI = R3 - RT$

Using the trigonometric identities $$\sin(R3 - RT) = \sin R3 * \cos RT - \cos R3 * \sin RT$$

and $$\cos(R3 - RT) = \cos R3 * \cos RT + \sin R3 * \sin RT$$

and using $$RT = \frac{RS}{N-1}*\left(\frac{N-1}{2} - I\right),$$

equations (9) and (10) can be rewritten $$X \text{ Rate} = K1 * (\cos R3 * \cos RT + \sin R3 * \sin RT) \quad \text{Eq. (11)}$$

$$Y \text{ Rate} = K2 * (\sin R3 * \cos RT - \cos R3 * \sin RT) \quad \text{Eq. (12)}$$

Figure 9:
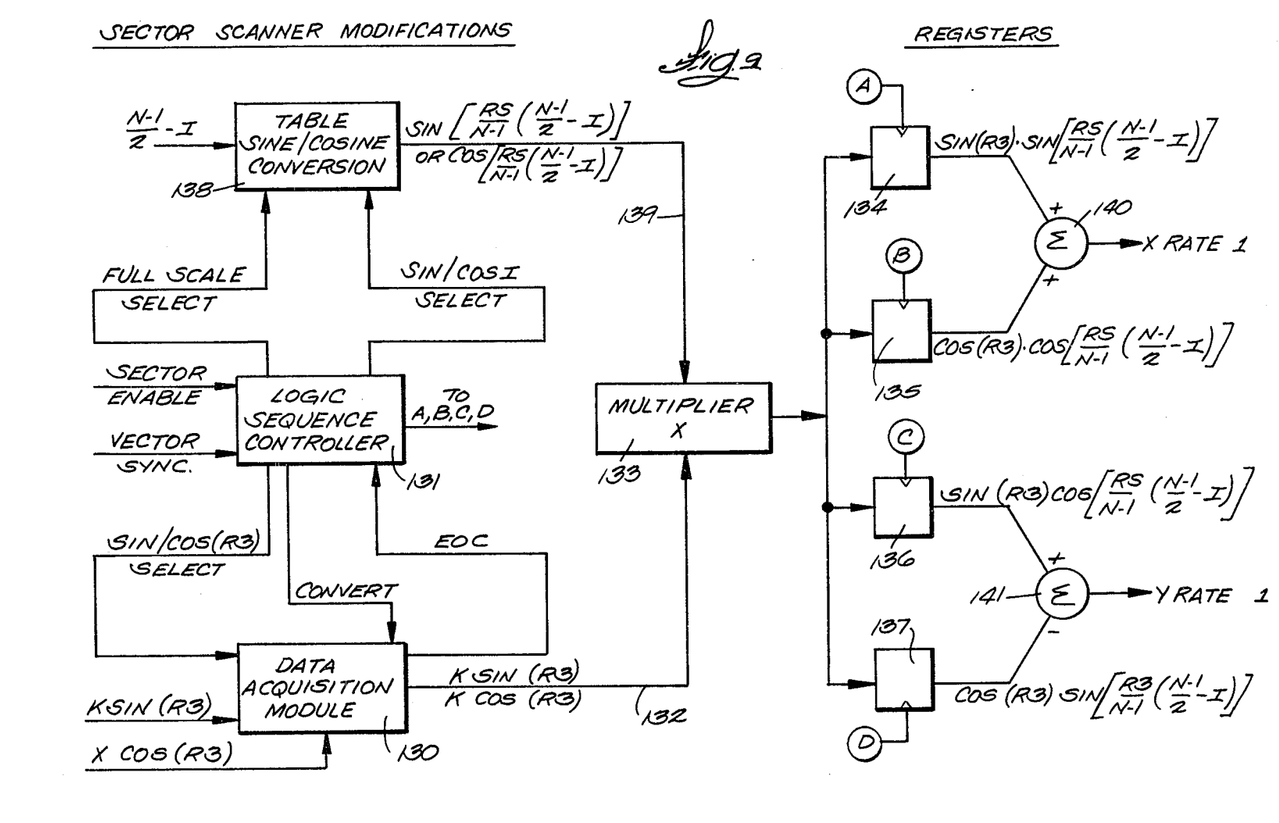
FIG. 9 is an electrical block diagram of a system that modifies the transducer direction information to the memory array storage controls for producing a composite picture with a sector scan or phased array transducer.

The manner in which the circuitry must be modified for sector scanning is illustrated in the FIG. 9 block diagram.

For sector scanning, equations (9) and (10) or (11) and (12) must be used to modify the apparent vector direction and, hence, the X-axis and Y-axis rate, namely, X Rate and Y Rate. In this illustration use of equations (11) and (12) is preferable since the values of Cos (R3) and Sin (R3) are available from that part of the circuitry shown in FIG. 7.

In FIG. 9, the scaled values for X Rate and Y Rate are used after they are converted to digital format in data acquisition module 130. This module, under control of the logic sequence controller module 131, selects as input either K Sin (R3) or K Cos (R3) and converts these analog inputs to digital words. By way of bus 132 these digital words are input to a digital multiplier 133. The output of multiplier 133 is stored in registers 134–137 for ultimate combination into new X Rate and Y Rate values.

The digital output from down counter 62 of FIG. 7, that is, [(N−1)/2−I] which identifies the angle of the beam that is active at the moment of a vector sync pulse is input to a digital conversion table 138 in FIG. 9. The output of this table on bus 139 is either the value $$\sin\left[\frac{RS}{N-1}*\left(\frac{N-1}{2} - I\right)\right]$$

or $$\cos\left[\frac{RS}{N-1}*\left(\frac{N-1}{2} - I\right)\right]$$

Which value is output depends upon the selection made by logic sequence controller 131. The table output on bus 139 is input to the other input of multiplier 133. The result of these operations is that, under control of sequence controller 131, the output of multiplier 133 can be any of the four terms needed for Equations (11) and (12). The sequence, initiated by each vector sync pulse delivered to logic sequence controller 131 may be as follows:

(a) Select K* Sin (R3) for conversion in data acquisition module 130.
(b) Select the sine output of table 138.
(c) Wait for end-of-conversion (EOC) signal from the data acquisition module 130.

(d) Wait for the multiplier 133 output to stabilize.

(e) Produce pulse (A) to save the multiplier 133 output in register 134.

(f) Select cosine output of the table 138.

(g) Wait for the multiplier 133 to stabilize.

(h) Produce pulse (C) to save the result in register 136.

(i) Select K* Cos (R3) for conversion in data acquisition module 130.

(j) Wait for EOC from module 130.

(k) Wait for the multiplier 133 to stabilize.

(l) Produce pulse (B) to save the multiplier output in register 135.

(m) Select the sine output of table 138.

(n) Wait for the multiplier 133 to stabilize.

(o) Produce pulse (D) to save the output in register 137.

The outputs from registers 134 and 135 are input to a summer 140. The sum obtained in summer 140 is the new X Rate. The outputs of registers 136 and 137 are input to a summer 141. The difference obtained in summer 141 is the new Y Rate. The X Rate and Y Rate signals are used in FIG. 4 for sector scanning as previously explained for the linear array transducer case.

The sector mode of operation can be converted to normal B-scan or linear array operation by inducing the logic sequence controller 131 to force the table 138 to a full scale output equal to one if the sector mode is not enabled. The multiplier 133 output is then just the input from data acquisition module 130 and X Rate 1 equals X Rate and Y Rate 1 equals Y Rate. The normal sequence can then proceed.

An alternative to using multiplier 133 as in the FIG. 9 example is to compute modified X Rate 1 and Y Rate 1 by using Equations (9) and (10). This method uses the linear angle R3 in the computations rather than the sine and cosine of R3. Both functions are needed, however, to determine the quadrant of the distal arm angle R3.

Referring to FIG. 10, the analog signal data Sin (R3) is converted to digital data by the A/D converter 145 under the control of a logic controller 146. The digital data is then used to find the scaled angle in a table 147. The offset of the angle depends on the quadrant it is in, and the logic controller determines this by detecting the outputs of comparators 148 and 149. The comparators compare the data Sin (R3) and Cos (R3) to zero to determine their signs and, thus, the quadrant of R3.

The data from table 147 is summed in a summer 148 with the digital output signal of down counter 62 of FIG. 7 to yield the term [R3*(N−1)/RS]−[(N−1)/2−I] which is the angle RI* (N−)/RS.

The latter angle is input to a sine table and a cosine table 150 to find the sine and cosine of the unscaled angle RI. The values Sin (RI) and Cos (RI) are multiplied by the particular rate needed for the specific scale factor for the memory array by converting the signals back to analog in D/A converters 151 and 152 and then amplifying them with gain K in amplifiers 153 and 154. The output of amplifiers 153 and 154 are then the modified X Rate 1 and Y Rate 1 in analog form and these signals are used as previously discussed in connection with FIG. 4.

X Rate 1 and Y Rate 1 in the FIG. 10 embodiment can be made equal to X Rate and Y Rate, as one example, by multiplexing the analog outputs from D/A converters 151 and 152 with the actual values of Sin (R3) and Cos (R3) although the elements for performing these functions are not shown in FIG. 10. This would, however, permit non-sector scan operation.

Although implementations of the composite real-time and static image display invention have been described in detail, such descriptions are intended to be illustrative rather than limiting for the invention may be variously implemented and is to be limited only by construing the claims which follow.

We claim:

1. An ultrasound imaging system for displaying static and real-time images simultaneously comprising:
   a transducer unit including a linear array of juxtaposed transducer elements having their end faces lying substantially in a common plane, said elements being subject to activation in a predetermined order for projecting ultrasound beam pulses into a body and receiving echos originating at impedance discontinuity points in the body, said elements converting the echos to electric echo signals corresponding to the intensities of the echos, the lines along which the beams and echos travel being designated as vectors,
   a base,
   an articulated arm assembly including proximal, intermediate and distal arm members, the proximal member being pivotally mounted to the base and the distal member being pivotally connected to an intermediate member, the length of the transducer element array being arranged perpendicular to the length of said distal arm and the distance from the pivot axis of the distal arm to the end face at the center of the array constituting the total length of the distal arm member, said arm assembly supporting said transducer unit and constraining it to move and transmit said beams in a single selected plane,
   a memory array having input means for said echo signals, said array having locations to which the echo signals are addressable in correspondence to locations in the body from which the signals originate, and having address input means,
   means for generating repeatable sequences of vector sync pulses, the first pulse in a sequence initiating a frame,
   means for activating said transducer elements to transmit said beam pulses, said means for activating responding to occurrence of the sync pulses by activating the elements in said predetermined order,
   means for developing signals, respectively, representative of the X and Y coordinates of the center of the linear array,
   means for developing signals, respectively, representative of the distances in the X and Y directions of the currently active transducer element from the center of the linear array,
   means for summing the signals representative of said X coordinate and X distance and means for summing the signals representative of said Y coordinate and Y distance to thereby yield discrete signals representing, respectively, the X and Y position coordinates of the active transducer element,
   means for developing signals representative of the rate of change of the distance of the echos in the X and Y directions from the active element in respect to time as the echos are being returned to the active transducer from the point where the echo originates, means responsive to said signals representative of said rate of change by developing signals representative of the distance of said points in the X and Y directions from said X and Y positions coordinates of the active transducer element, means responding to the signals representative of the X and Y positions of the active transducer element and the signals representative of the distance of said points from said X and Y positions by producing addresses that are coupled to said address input means for storing the echo representative signals corresponding to picture elements in memory array locations along vectors corresponding to the locations at which the echos originate in the body to thereby store pixels composing an image frame corresponding to the present position of said transducer to thereby provide for a real-time display of the image presently in the plane of the transducer array, movement of said transducer resulting in said locations being no longer addressed so as to result in static storage of the real-time image preceding said movement whereupon a new set of addresses are generated for the real-time image frame corresponding to the position in which said transducer has been moved, and means for displaying the static stored image and the real time image simultaneously.

2. Ultrasound scanning apparatus adapted for simultaneous display of contiguous static and real-time images of a layer in a body comprising:

a transducer unit comprised of a linear array of juxtaposed transducer elements having corresponding end faces disposed in a substantially common plane, pulser and receiver means for activating said transducer elements in a predetermined order to respectively project ultrasound beam pulses into said body along vectors and to convert echos returned to the elements to electric signals corresponding to impedance discontinuities in the body from which the echos originate, a memory array for storing the signals corresponding to echos in locations along vectors that correspond to said vectors in the body, said memory array having address input means and echo signal input means, means for generating repeatable sequences of vector sync pulses, the first pulse in a sequence initiating a frame, said pulser and receiver means responding to occurrence of said vector sync pulses by causing said transducer elements to project the ultrasound beam pulses in a predetermined order, a base, an articulated arm assembly including a proximal arm member of length L1 pivotally connected to the base, at least one intermediate arm member of length L2 pivotally connected to the proximal arm member, and a distal arm member to which the transducer unit is mounted, the length L3 of the distal arm constituting the distance from its pivot to the face of the array at the center, said arm assembly providing for moving said unit over said body in a single selected plane, the angles of said arms of lengths L1, L2 and L3 with respect to horizontal being designated, respectively, R1, R2 and R3, means for providing signals representative of the sines of the angles R1, R2 and R3 respectively and of the cosines of the angles R1, R2 and R3, means for amplifying the signals representative of the sines of R1, R2 and R3 by the length of the arms L1, L2 and L3 respectively to thereby provide signals whose sum is representative of the X-position coordinate of the center of the array, means for amplifying the signals representative of the the cosines of R1, R2 and R3 respectively by the length of the arms L1, L2 and L3 to thereby provide a signals whose sum is representative of the Y-position coordinate of the center of the array, means for producing a first signal corresponding to the sine of R3 multiplied by $L4/N-1$ where L4 is the length of the element array and N is the number of elements in the array, means for producing a second signal corresponding to the cosine of R3 multiplied by $L4/N-1$, a down counter having input means for a number $N-1/2$ representative of the number of vector sync pulses required to activate the elements from an end to the center of the array, said counter being operative to decrement said number upon occurrence of each vector sync pulse in a sequence and to output corresponding digital number corresponding to $N-1/2=i$ where i is the number of decrements, digital-to-analog converter means for converting said digital numbers to corresponding successive analog signals, multiplier means for multiplying said first signal by said analog signals in succession to yield third signals representative of the X direction displacement of the transducer element being activated from the center of the array, means for summing said third signals with said signal that represents the X position coordinate of the center of the array to yield a fourth signal corresponding to the X position coordinates of the transducer element which is active, another multiplier means for multiplying said second signal by said analog signals in succession to yield fifth signals representative of the Y direction displacement of the transducer element being activated from the center of the array, means for summing said fifth signals with said signal that represents the Y position coordinate of the center of the array to yield a sixth signal corresponding to the Y position coordinates of the transducer element which is active, means for developing signals representative of the rate of change of the distance of the echos in the X and Y directions from the active element in respect to time, respectively, as the echos are being returned to the active transducer from the point where the echo originates, means responding to said fourth and sixth signals that represent the X and Y positions of the active transducer element and to said signals representative of said rates of change in the distance from said X and Y positions by producing addresses that are coupled to said address input means for storing said echo representative signals corresponding to picture elements in memory array locations along vectors corresponding to locations at which the echos originate in the body to thereby store pixels composing an image frame corresponding to the present position of said transducer to thereby provide for a real-time display of the image presently in the plane of the transducer array, movement of said transducer resulting in said locations being no longer addressed so as to result in static storage of the real-time image preceding said movement whereupon a new set of addresses are generated for the real-time image frame corresponding to the position in which said transducer has been moved, and means for displaying a real-time image corresponding to the stored echo representative signals obtained while said transducer is in its present position and for simultaneously displaying a contiguous static image corresponding to echo signals obtained when said unit was in a previous position.

* * * * *